(12) United States Patent
Nash

(10) Patent No.: US 7,351,199 B2
(45) Date of Patent: Apr. 1, 2008

(54) CATHETERS

(75) Inventor: John Edward Nash, Hythe (GB)

(73) Assignee: Smiths Group PLC, London (GB)

( * ) Notice: Subject to any disclaimer, the term of this patent is extended or adjusted under 35 U.S.C. 154(b) by 756 days.

(21) Appl. No.: 10/636,775

(22) Filed: Aug. 8, 2003

(65) Prior Publication Data

US 2004/0039247 A1   Feb. 26, 2004

(30) Foreign Application Priority Data

Aug. 23, 2002   (GB) ................................ 0219779.6

(51) Int. Cl.
*A61D 7/00* (2006.01)
(52) U.S. Cl. .......................................................... 600/35
(58) Field of Classification Search ............ 600/33–35; 606/20–23; 604/6.13, 43, 113–114, 171, 604/523, 540, 6, 13
See application file for complete search history.

(56) References Cited

U.S. PATENT DOCUMENTS

| 3,698,394 A | 10/1972 | Piper et al. |
| 5,063,994 A * | 11/1991 | Verkaart .................... 165/154 |
| 5,437,673 A | 8/1995 | Baust et al. |
| 5,542,928 A | 8/1996 | Evans et al. |
| 6,149,673 A * | 11/2000 | Ginsburg .................... 607/96 |
| 2002/0111584 A1 | 8/2002 | Walker et al. |

FOREIGN PATENT DOCUMENTS

| WO | WO 01/58397 | 8/2001 |
| WO | WO 02/35924 | 5/2002 |
| WO | WO 02/47577 | 6/2002 |

\* cited by examiner

*Primary Examiner*—John P Lacyk
(74) *Attorney, Agent, or Firm*—Louis Woo

(57) ABSTRACT

An embryo transfer catheter or the like has electrical resistance heating elements extending along its shaft and connected to a battery in the catheter hub or to a separate power source via a cable. Alternatively, the shaft may be extruded with two channels in its wall connected with inlet and outlet connectors on the hub. Pipes connected with the connectors supply warmed fluid from a heat exchanger to one channel and return fluid to the exchanger from the other channel.

18 Claims, 2 Drawing Sheets

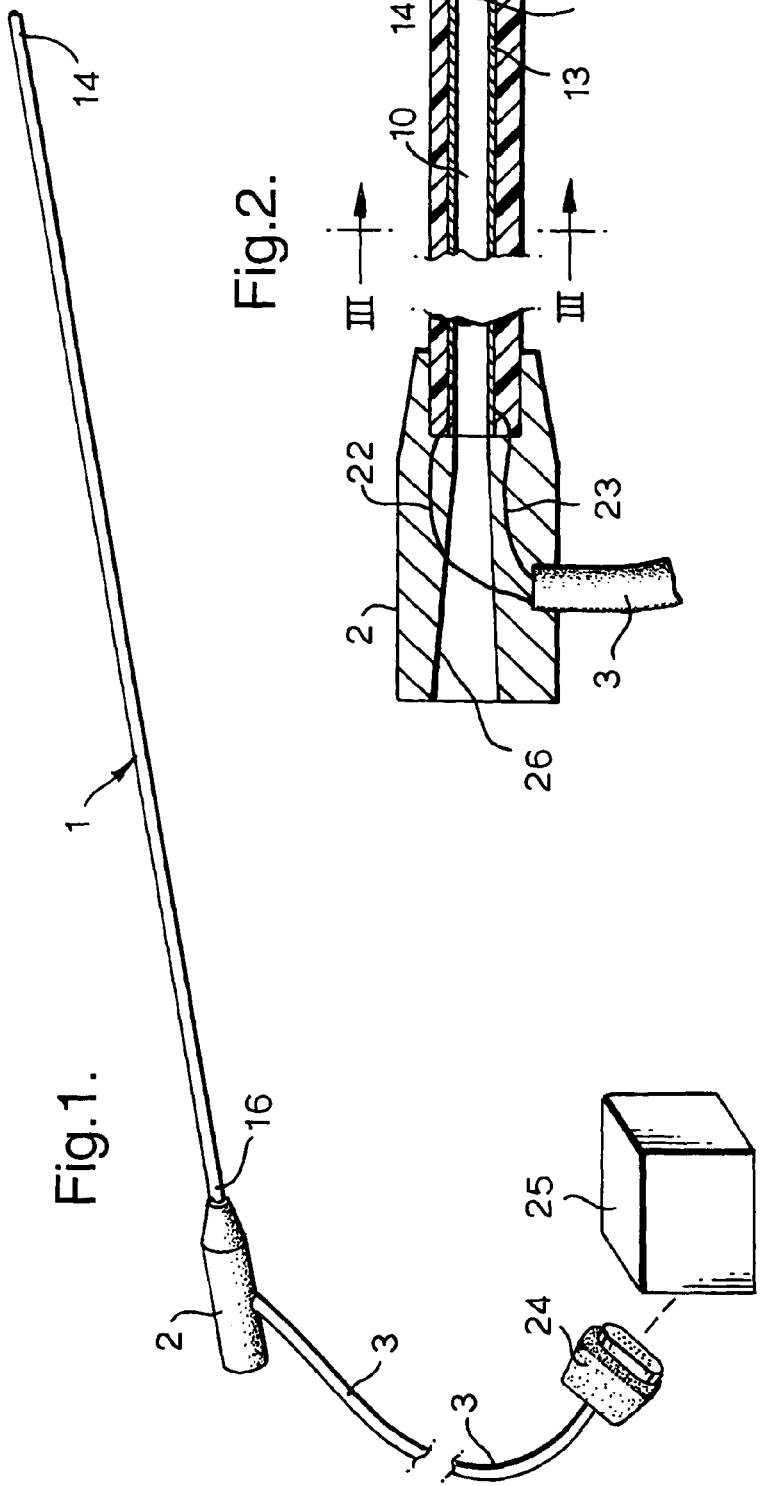
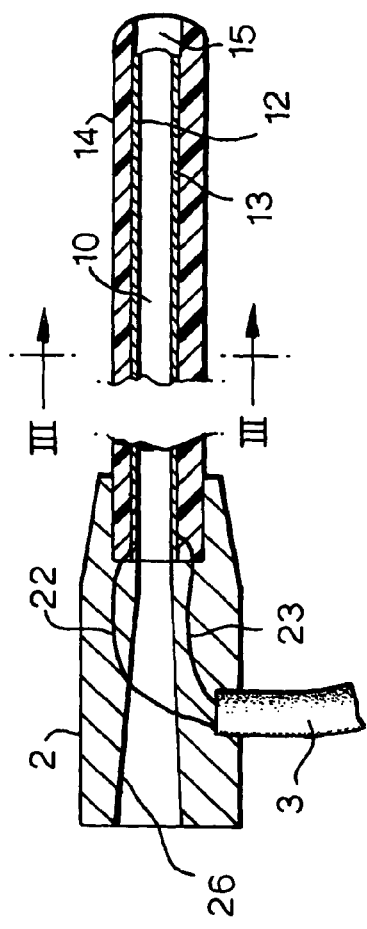
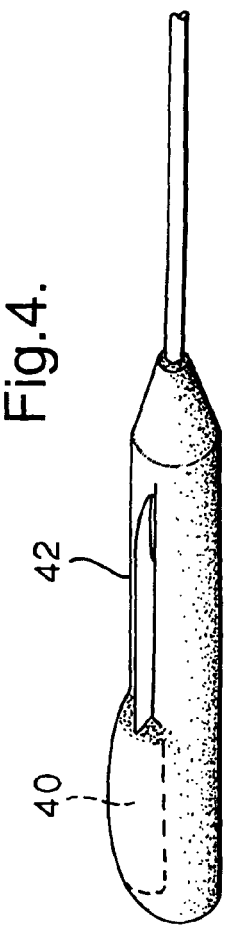
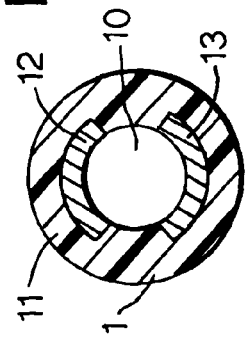

CATHETERS

BACKGROUND OF THE INVENTION

This invention relates to catheters.

An embryo transfer catheter is used to transport an embryo from a location where the embryo was fertilised to the woman in whom the embryo is to be transferred. One end of the catheter is inserted in the uterus and the embryo is expelled from the catheter to the uterus. The embryo is fertilised and grown under carefully controlled conditions in a culture medium, in particular, care is taken to keep the embryo at the correct temperature to encourage its growth. Although the embryo in the catheter is transported as quickly as possible, there can often be delays in transferring the embryo to the patient. In particular, if the position of the uterus is found to be difficult, the surgeon may need to undertake additional procedures before the catheter can be inserted. This can delay insertion of the embryo and may cause its temperature to drop while the catheter is exposed to room temperature. Similar problems arise with oocyte recovery catheters used to transfer oocytes from a woman for in vitro fertilisation or other treatment.

BRIEF SUMMARY OF THE INVENTION

It is an object of the present invention to provide a catheter that will help maintain the desired temperature of an embryo or oocyte.

According to one aspect of the present invention there is provided a catheter for use in handling an embryo or oocyte, the catheter including heating means for heating the catheter.

The heating means may be electrical heating means such as including an electrical resistance heating element extending along a part at least of the length of the catheter. The heating element may be an extruded stripe of an electrically-conductive plastics material, such as of PVC loaded with an electrically-conductive material. The heating element may extend along the bore of the catheter. The catheter may include a hub at its machine end, the hub having a female tapered bore opening into the interior of the catheter and an electrical cable extending therefrom terminated by an electrical connector. The catheter may include a battery located in a hub at the machine end of the catheter. Alternatively, the catheter may include a fluid passage extending along a part at least of the length of the catheter by which fluid at a regulated temperature can be supplied to warm the catheter. The channel is preferably formed within the thickness of the wall of the catheter and may be extruded with the wall of the catheter. The catheter preferably has two channels located diametrically opposite one another arranged so that fluid supplied to one channel flows from the machine end towards the patient end and back along the other channel from the patient end to the machine end. The or each channel is preferably of arcuate shape According to another aspect of the present invention there is provided a system including an embryo or oocyte catheter having an electrical resistance heating element extending along a major part of its length, a cable connected with the heating element and an electrical power source connected with the cable so that the catheter can be heated.

According to a further aspect of the present invention there is provided a system including an embryo or oocyte catheter having two fluid channels extending along a major part of its length, pipes connected with respective channels and a heat exchanger by which fluid can be warmed and supplied to the catheter via one of the pipes, the fluid returning to the heat exchanger via the other of the pipes.

Examples of embryo transfer catheter systems according to the present invention, will now be described, by way of example, with reference to the accompanying drawings.

BRIEF DESCRIPTION OF THE DRAWINGS

FIG. 1 is a perspective view of a system including one form electrically-heated catheter;

FIG. 2 is a sectional, side elevation view of the catheter of FIG. 1 to a larger scale;

FIG. 3 is a transverse sectional view of the catheter along the line III-III of FIG. 2;

FIG. 4 is a perspective view of a part of an alternative electrically-heated catheter;

DETAILED DESCRIPTION OF THE PREFERRED EMBODIMENTS

Figure 5:
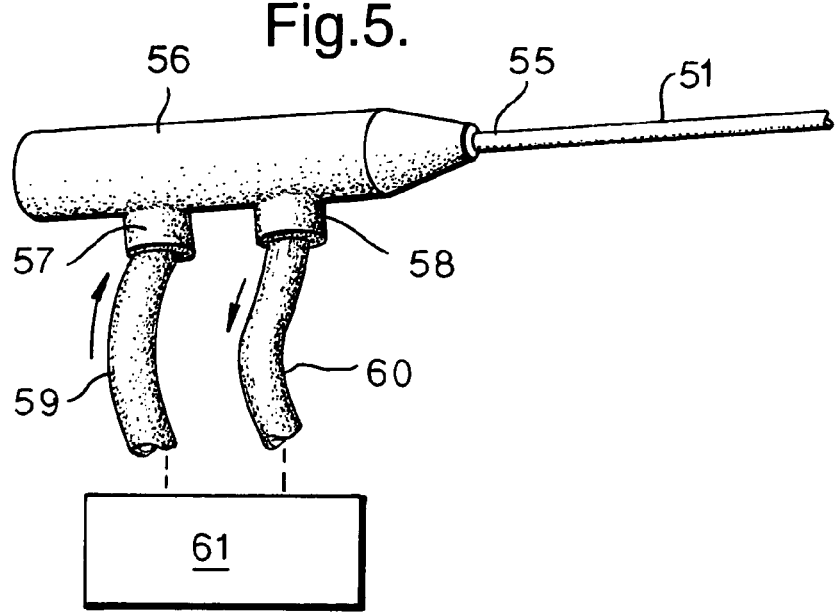
FIG. 5 is a perspective view of a system including an alternative, fluid-heated catheter.

With reference first to FIGS. 1 to 3, the system includes a catheter comprising a flexible hollow shaft 1, a hub 2 at its machine end and an electrical cable 3 extending from the side of the hub.

The shaft 1 is extruded from a plastics material, such as PVC, and is of circular section with a bore 10 extending along its entire length. The outer part 11 of the shaft 1 is of a conventional, electrically-insulating material but the shaft also has two extruded stripes 12 and 13 of an electrically-conductive plastics extending along the shaft. The stripes 12 and 13 are preferably of PVC loaded with an electrically-conductive material, such as carbon. The stripes 12 and 13 extend along the bore 10 and are electrically isolated from one another along most of their length. At the patient end 14 of the shaft 1, the two stripes 12 and 13 electrically connect with one another via a bridge 15. The bridge 15 may take various forms, such as a separate member of electrically-conductive material inserted in the catheter or the material of the stripes 12 and 13 flowed into one another by heating. The two stripes 12 and 13 provide an electrical resistance heating element extending from the machine end 16 to the patient end 14 and back again. There are various alternative ways in which an electrical resistance heating element could be provided. The stripes could be of various different configurations and could be extruded within the wall of the shaft, or on its outside, so that they do not directly contact material within the bore of the catheter. The heating element could be provided by a metal wire embedded into the outside of the catheter.

At its machine end, the stripes 12 and 13 are electrically connected with the cable 3. The cable 3 has two wires 22 and 23 within it that extend through the hub 2 and connect with the stripes 12 and 13. A connector 24 terminates the end of the cable 3 remote from the hub 2. This connector 24 makes connection with an electrical power source 25 forming a part of the system.

The hub 2 has a female luer taper bore 26, for receiving the nose of a syringe or the like, and opens into the bore 10 of the shaft 1.

The heating provided by the catheter may be temperature regulated, such as by making the heating elements of a positive temperature coefficient material or by incorporating a temperature sensor within the catheter providing a temperature feedback signal to the power source 25. Alternatively, the heating may be unregulated, the resistance of the heating element and the power source being arranged to ensure that the maximum heating that can be provided is below a level that could cause damage to the embryo. Preferably, the heating is arranged to maintain the temperature of the catheter close to the ideal temperature for the embryo, around 37° C.

Instead of using an external power source to provide power for the resistance heating element, this could be provided by a battery 40 built into a modified hub 42 of the catheter, as shown in FIG. 4.

Figure 6:
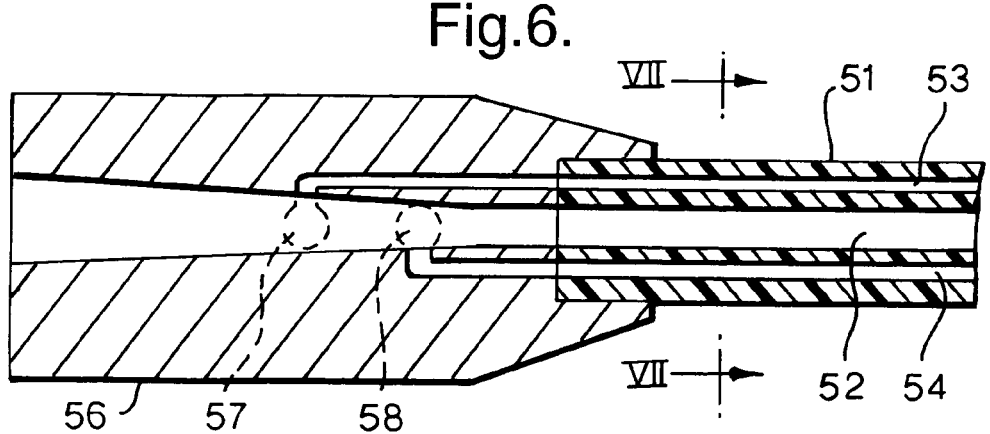
FIG. 6 is a sectional side elevation view of the catheter of FIG. 5.
Figure 7:
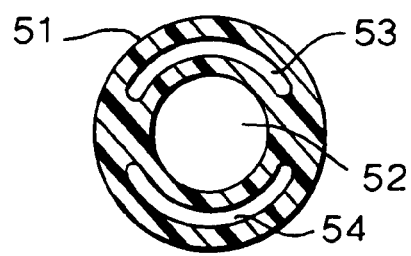
FIG. 7 is a transverse sectional view of the catheter of FIGS. 5 and 6 along the line VII-VII of FIG. 6.

With reference now to FIGS. 5 to 7 there is shown an alternative catheter system having a catheter heated by flow of fluid along it. The catheter has a flexible shaft 51 extruded of PVC with a central bore 52 for receiving the embryo and its transfer medium. The shaft 51 also has two side channels 53 and 54 of arcuate shape extending coaxially around the central bore diametrically opposite one another, the side channels being for passage of the heating fluid. At the patient end of the catheter (not shown), the two channels 53 and 54 connect with each other so that fluid flows along one channel 53 in one direction and then flows along the other channel 54 in the opposite direction. At the machine end 55, the catheter has a hub 56 with an inlet connector 57 and an outlet connector 58; passages within the hub connect the inlet and outlet with respective ones of the channels 53 and 54. The connectors 57 and 58 are connected by respective pipes 59 and 60 with a heat exchange unit 61 forming a part of the system. The unit 61 includes a heater, a temperature control and a pump that pumps water, or some other fluid, through the heater to the inlet connector 57. Warmed water flows along the channel 53 from the machine end 55 to the patient end and then back down the other channel 54 from the patient end to the machine end where it emerges from the outlet connector 58 and flows to the inlet of the pump in the heat exchanger unit 61.

It will be appreciated that the channels for heating fluid could have different sections, need not extend in a straight path along the catheter and need not extend along the entire length of the catheter.

The catheter of the present invention enables the embryo or oocyte to be maintained at an optimum temperature for prolonged periods within the catheter if, for example, there were delays in handling the sample.

I claim:

1. A catheter for use in handling an embryo or oocyte, wherein the catheter has a bore extending along its length and opening in the region of its patient end, wherein the bore is adapted for containing an embryo or oocyte, and wherein the catheter includes a heater for heating the bore through the catheter and the contents of the bore.

2. A catheter according to claim 1, wherein said heater is an electrical heater.

3. A catheter according to claim 2, wherein said heater includes an electrical resistance heating element extending along a part at least of the length of the catheter.

4. A catheter according to claim 3, wherein said heating element is an extruded stripe of an electrically-conductive plastics material.

5. A catheter according to claim 4 wherein said extruded stripe is of PVC loaded with an electrically-conductive material.

6. A catheter according to claim 3, wherein said heating element extends along a bore of the catheter.

7. A catheter according to claim 2 including a hub at its machine end, wherein said hub has a female tapered bore opening into an interior of the catheter and an electrical cable extending therefrom terminated by an electrical connector.

8. A catheter according to claim 2 including a battery located in a hub at a machine end of the catheter.

9. A catheter according to claim 1, wherein the heater includes a fluid passage extending along a part at least of the length of the catheter by which fluid at a regulated temperature can be supplied to warm the catheter.

10. A catheter according to claim 9, wherein said fluid passage is a channel formed within the thickness of a wall of the catheter.

11. A catheter according to claim 10, wherein said channel is extruded with said wall of the catheter.

12. A catheter according to claim 10, wherein the catheter has two channels located diametrically opposite one another arranged so that fluid supplied to one channel flows from a machine end towards a patient end and back along the other channel from said patient end to said machine end.

13. A catheter according to claim 10, wherein said channel is of arcuate shape.

14. A system comprising: an embryo or oocyte catheter having a bore extending along its length for containing an embryo or oocyte, said bore opening in the region of the patient end of the catheter and being adapted for containing an embryo or oocyte, and the catheter having an electrical resistance heating element extending along a major part of its length such as to heat a major part of the length of the bore; a cable connected with said heating element; and an electrical power source connected with said cable so that the bore along the catheter can be heated.

15. A system comprising: an embryo or oocyte catheter having a bore extending along its length for containing an embryo or oocyte, said bore opening in the region of the patient end of the catheter and being adapted for containing an embryo or oocyte, and the catheter having two fluid channels extending along a major part of its length; two pipes connected with respective ones of said channels; and a heat exchanger connected with said pipes by which fluid can be warmed and supplied to the catheter via one of said pipes, and wherein said fluid returns to said heat exchanger via the other of said pipes.

16. A catheter for use in handling an embryo or oocyte comprising: a plastic shaft, said shaft having a bore extending along its length and opening at a patient end for receiving an embryo or oocyte; an electrical resistance heating element extending along said shaft; a hub attached to a machine end of said shaft with a patient end of said shaft by which material can be supplied to or from the bore of the shaft; and an electrical cable connected at one end with said heating element and connected at its other end with an electrical connector so that the bore of the catheter can be heated by connecting the connector to a source of electrical power.

17. A catheter for use in handling an embryo or oocyte comprising: a plastic shaft, said shaft having a bore extending along its length and opening at a patient end for receiving an embryo or oocyte; an electrical resistance heating element extending along said shaft; a hub attached to a machine end of said shaft with a patient end of said shaft by which material can be supplied to or from the bore of the shaft; and a battery within the hub connected with said heating element so that the bore of the catheter can be heated by said battery.

18. A catheter for use in handling an embryo or oocyte comprising: a plastic shaft, said shaft having a bore extending along its length and opening at a patient end: two fluid channels extending along said shaft, said channels being interconnected towards said patient end for receiving an embryo or oocyte; a hub attached to a machine end of said shaft with a patient end of said shaft by which material can be supplied to or from the bore of said shaft; an inlet and outlet connector on said hub; and a fluid connection between said channels and respective ones of said connectors by which warmed fluid can be supplied to one of said channels to flow towards said patient end of said shaft and to flow back towards said hub along the other of said channels so as to warm the bore of the catheter.

* * * * *